US009063138B2

(12) United States Patent
Chen et al.

(10) Patent No.: US 9,063,138 B2
(45) Date of Patent: Jun. 23, 2015

(54) DEVICE AND METHOD FOR INDIRECT ELECTRONIC CONDITION CONTROL IN BIOMOLECULE DETECTION PLATFORMS

(75) Inventors: Michael Chen, Sunnyvale, CA (US); Vincent Chen, Stanford, CA (US); Sam Kavusi, Menlo Park, CA (US); Christoph Lang, Cupertino, CA (US)

(73) Assignee: Robert Bosch GmbH, Stuttgart (DE)

( * ) Notice: Subject to any disclaimer, the term of this patent is extended or adjusted under 35 U.S.C. 154(b) by 248 days.

(21) Appl. No.: 13/348,727

(22) Filed: Jan. 12, 2012

(65) Prior Publication Data
US 2012/0115236 A1    May 10, 2012

Related U.S. Application Data

(63) Continuation-in-part of application No. 12/580,113, filed on Oct. 15, 2009.

(51) Int. Cl.
G01N 33/53 (2006.01)
G01N 33/543 (2006.01)
C08F 20/56 (2006.01)

(52) U.S. Cl.
CPC .......... *G01N 33/54393* (2013.01); *Y10T 436/11* (2015.01); *Y10T 436/115831* (2015.01); *C08F 20/56* (2013.01); *G01N 33/5306* (2013.01)

(58) Field of Classification Search
CPC ........... B01D 15/3804; B01D 15/3809; B01D 15/3861–15/3885; C07K 1/22
USPC .............. 422/105, 107–111; 424/1.25; 435/3, 435/286.1; 436/50, 55; 524/916
See application file for complete search history.

(56) References Cited

U.S. PATENT DOCUMENTS

| 6,696,258 B1 * | 2/2004 | Wei et al. ................ 435/7.2 |
| 7,348,783 B1 | 3/2008 | Hsiung et al. |
| 2005/0025820 A1 * | 2/2005 | Kester et al. ................ 424/450 |
| 2005/0169882 A1 * | 8/2005 | Lowe et al. ................ 424/78.27 |
| 2009/0155571 A1 * | 6/2009 | Mustonen ................ 428/327 |
| 2009/0190135 A1 | 7/2009 | Clarizia et al. |

(Continued)

FOREIGN PATENT DOCUMENTS

| CN | 101 857 666 A | 10/2010 |
| KR | 2011 0129725 A | 12/2011 |

(Continued)

OTHER PUBLICATIONS

International Search Report in correspondence PCT application (i.e., PCT/US2013/021133), mailed Apr. 24, 2013 (14 pages).

(Continued)

*Primary Examiner* — Melanie Y Brown
*Assistant Examiner* — Erik B Crawford
(74) *Attorney, Agent, or Firm* — Maginot Moore & Beck LLP

(57) ABSTRACT

A system and method of indirectly modifying an environmental condition at a test site in one embodiment includes providing a test site on a substrate, providing a hydrogel composition loaded with a chemical factor at the test site, providing an actuator configured to activate the hydrogel composition to release a chemical factor at the test site, controlling the actuator to activate the hydrogel composition to release a chemical factor at the test site, and modifying the local chemical environment at the test site with the chemical factor.

19 Claims, 6 Drawing Sheets

(56) References Cited

U.S. PATENT DOCUMENTS

| | | |
|---|---|---|
| 2011/0091870 A1 | 4/2011 | Lang et al. |
| 2011/0195853 A1 | 8/2011 | Kavusi et al. |
| 2011/0208021 A1* | 8/2011 | Goodall et al. ............... 600/309 |

FOREIGN PATENT DOCUMENTS

| | | |
|---|---|---|
| WO | 2009146147 A2 | 12/2009 |
| WO | 2011143188 A1 | 11/2011 |

OTHER PUBLICATIONS

Guenther et al., "Biochemical microsensors on the basis of metabolically sensitive hydrogels", Proceedings of SPIE; Mar. 24, 2011; pp. 79762D-2-79762D-9; vol. 7976; Germany and USA (9 pages).

Kaetsu, "Biomedical Materials, Devices and Drug Delivery Systems by Radiation Twxhniques", Radiation Physics and Chemistry; Mar. 1, 1996; pp. 419-424; vol. 47, No. 3; Elsevier Science Publishers BV; The Netherlands (6 pages).

Sutani et al., "The synthesis and the electric-responsiveness of hydrogels entrapping natural polyelectrolyte", Radiation Physics and Chemistry; Jun. 27, 2000; pp. 49-54; vol. 61, No. 1; Elsevier Science Publishers BV; The Netherlands (6 pages).

Hood, Leroy, et al., "Systems and Biology and New Technologies Enable Predictive and Preventive Medicine," Science 306, No. 5696, Oct. 22, 2004; pp. 640-643.

Service, Robert F., "Proteomics:" Proteomics Ponders Prime Time, Science 321, No. 5897, Sep. 26, 2008, pp. 1758-1761.

Kingsmore, Stephen F., "Multiplexed Protein Measurement: Technologies and Applications of Protein and Antibody Arrays," Nature Reviews, Drug Discovery 5, No. 4, Apr. 2006, pp. 310-320.

Liotta, Lance A. et al., "Protein Microarrays: Meeting Analytical Challenges for Clinical Applications," Cancer Cell 3, No. 4, Apr. 2003, pp. 317-325.

Sosnowski, R.G., et al., "Rapid Determination of Single Base Mismatch Mutations in DNA Hybrids by Direct Electric Field Control," Proceedings of the National Academy of Sciences of the United States of America 94, No. 4, Feb. 18, 1997.

Wong, Ian Y. and Melosh, Nicholas A., "Directed Hybridization and Melting of DNA Linkers Using Counterion-Screened Electric Fields," Nano Letters 0, No. 0, January.

Wong, Ian Y., Footer, Matthew J. and Melosh, Nicholas A., "Electronically Activated Actin Protein Polymerization and Alignment," Journal of the American Chemical Society 130, No. 25, Jun. 1, 2008, pp. 7908-7915.

Ulrich, Rant et al., "Switchable DNA Interfaces for the Highly Sensitive Detection of Label-Free DNA Targets," Proceedings of the National Academy of Sciences 104, No. 44, Oct. 30, 2007, pp. 17364-17369.

Kamath, K. and Park, K., "Biodegradable Hydrogels in Drug Delivery," Advanced Drug Delivery, vol. 11, pp. 59-84, 1993.

Qiu, Y. and Park, K., "Environment-Sensitive Hydrogels for Drug Delivery," Advanced Drug Delivery, vol. 53, pp. 321-339, 2001.

Firestone, B. and Siegel, R., "Kinetics and Mechanisms of Water Sorption in Hydrophobic, Ionizable Copolymer Gels," Journal of Applied Polymer Science, vol. 43, 1991.

Tanaka, T., Nishio, I. Sun, S. and Ueno-Nichio, S., "Collapse of Gels in an Electric Field," Science, vol. 218, 1982.

Lee, K., Cussler, E., Marchetti, M. and McHugh, M., "Pressure-Dependent Phase Transitions in Hydrogels," Chemical Engineering Science, vol. 45, pp. 766-767, 1990.

Linden, H. J. v. d., Herber, S., Olthuis, W. and Bergveld, P., "Stimulus-Sensitive Hydrogels and Their Applications in Chemical (Micro)Analysis," The Analyst, vol. 128, pp. 325-331, 2003.

Heskins, M. and Guilleit, J., "Solution Properties of Poly (N-Isopropylacrylamide)," Journal of Macromolecular Science Chemistry, vol. A2, pp. 1441-1455, 1958.

Dinarvand, R. and D'Emanuele, A., "The Use of Thermoresponsive Hydrogels for On-Off Release of Molecules," Journal of Controlled Release, vol. 36, pp. 221-227, 1995.

Khare, A. and Peppas, N., "Release Behavior of Bioactive PH-Sensitive Hydrogels," Journal Biomater Science Polymer, vol. 4, pp. 275-289, 1993.

Murdan, Sudaxshina, "Electro-Responsive Drug Delivery From Hydrogels," Journal of Controlled Release: Official Journal of the Controlled Release Society 92, No. 1-2, Sep. 19, 2003.

Bergveld,P., "Development of an Ion Sensitive Solid-State Device for Neurophysiological Measurements," IEEE Transactions on Biomedical Engineering, BME-17, pp. 70-71, 1970.

Hizawa, T., et al., "Fabrication of a Two-Dimensional PH Image Sensor Using a Charge Transfer Technique," Transducers 2005. pp. 509-515, 2006.

Kwon, Ick Chan, Bae, You Han and Kim, Sung Wan, "Electrically Erodible Polymer Gel for Controlled Release of Drugs," Letters to Nature, vol. 354, Nov. 28, 1991, pp. 291-293.

Bromberg, Lev E. and Ron, Eyal S., "Temperature-Responsive Gels and Thermogelling Polymer Matrices for Protein and Peptide Delivery," Advanced Drug Delivery, vol. 31, 1998, pp. 197-227.

* cited by examiner

DEVICE AND METHOD FOR INDIRECT ELECTRONIC CONDITION CONTROL IN BIOMOLECULE DETECTION PLATFORMS

PRIORITY

This application is a continuation-in-part of U.S. patent application Ser. No. 12/580,113 to Lang et al. and entitled "MULTISITE BIOSENSOR AND ASSOCIATED METHOD", filed Oct. 15, 2009, the entirety of which is incorporated herein by reference.

FIELD

This patent relates generally to controlling assay conditions in diagnostic tests and more specifically to multiplexed measurement platforms and diagnostic tests.

BACKGROUND

Personalized, preventative, predictive medicine demands diagnostic tests that can be performed at the point of care of an individual, with extreme fidelity that allows a caregiver or researcher to identify specific biomolecules even if those biomolecules are in low concentrations. While multiplexed measurement platforms, such as protein arrays, are utilized in research, there is a need in the art for a point of care platform that operates not only simply, but with great fidelity, as the concentration of different biomolecules in the blood can vary by more than ten orders of magnitude. As such, the identification of low concentration biomolecules, such as biomarkers of interest in certain diagnostic tests, requires that the affinity of the capture molecule to the low concentration biomolecule be orders of magnitude higher than any other molecule in the sample.

It will be appreciated that, depending upon the particular diagnostic test or assay, the substance tested may be human body fluids such as blood, serum, saliva, biological cells, urine, or other biomolecules. Additionally, testing may be further desired on consumables such as milk, plant tissues or extracts, baby food, or even water. As such there is a need in the art to provide a low cost multiplexed assay for target molecules with sufficient sensitivity and specificity.

Current attempts to provide such an assay or diagnostic test utilize affinity based sensors. Affinity based sensors function according to a "key-lock" principal in which a molecule with very high association factor to the marker of interest is used for detection. For example, a pregnancy test kit may incorporate a monoclonal antibody specific to a β-subunit of hCG (βhCG). The antibody is conjugated with a tag, e.g., gold, latex, or fluorophore, which is used for detection. If the targeted molecule binds with the conjugated antibody, the tagged pair is detectable such as by a visible test line.

Similarly, molecular tests based upon enzyme-linked immunosorbent assay ("ELISA") techniques utilize an antibody or antigen bound to a substrate to immobilize a target molecule. For example, FIG. 1 depicts an ELISA assay 10 wherein antibodies 12 are immobilized on a substrate 14. The substrate 14 may be positioned within a well (not shown). A blocker 16 is provided to cover the surface of the substrate around the antibody 12. In a typical ELISA assay, a sample is then added to the well in which the primary antibody 12 is immobilized. Next, the sample is incubated for some time. During incubation, the blocker 16 prevents the target molecules in the sample from binding to the surface of the substrate 14 in order to avoid false binding. During incubation, some of the target molecules 18 become bound with some of the antibodies 12 as depicted in FIG. 2. After incubation, the remaining sample is washed to remove the unbound primary antibodies 18.

Subsequently, a secondary antibody 20 with a bound label 22 is added to the well, incubated, and washed resulting in the configuration of FIG. 3. As depicted in FIG. 3, the labeled secondary antibodies 20 are bound to the target molecules 18 that are in turn bound to the antibodies 12. Accordingly, the number of labels 22 bound by the antibodies 20 to the antigen 18 is proportional to the concentration of the target antigen. Depending on the label used, the number of labels can be finally detected using colorimetry, amperometry, magnetometry, voltammetry, luminescence, or fluorescence detection. Other label-free antibody processes such as surface plasmon resonance may alternatively be used.

It will be appreciated that the reliability and minimum detectable concentration of a target molecule are directly related to the sensitivity and cross-reactivity of the detection assay. Indeed, as the cross-reactivity of the assay increases, the minimum detectable concentration and the diagnosis error rate increase. The sensitivity in such tests is generally limited by label detection accuracy, association factor of the antibody-antigen pair, and the effective density of the probe antibody on the surface.

As noted above, one issue that arises with affinity based sensors is the cross-reactivity of the sensor to other biomolecules. Indeed, in cross-reactive assays, a sensor tends to also sense biomarkers other than the biomarker of interest. The cross-reactivity issue is depicted in FIG. 4 wherein an ELISA assay 30 includes antibodies 32 immobilized on a substrate 34 to act as a capture molecule with a blocker 36 covering most of the substrate surface 34. Additionally, a labeled secondary antibody 38 is bound to a target molecule 40 which is in turn bound by the primary antibody 32. The labeled secondary antibody 38 has also bound to a molecule 42 which exhibited an affinity for the primary antibody 32 and was labeled by a secondary antibody 38. The sensitivity to a broad range of biomarkers thus increases the false negative/positive rate of diagnostic tests at clinical level as reported, for example, by P. A Benn et al., "Estimates for the sensitivity and false-positive rates for second trimester serum screening for Down syndrome and trisomy 18 with adjustment for cross identification and double positive results," *Prenatal Diagnosis*, Vol. 21, No. 1, pp 46-51, 2001. The presence of other molecules (secondary molecules or antigens) in the sample thus affects the minimum detectable concentration by binding to the primary antibody.

The accuracy of the assay may further be affected by physiosorption. As further depicted in FIG. 4, some features 44 present in the ELISA assay 30, either contaminants or simply an incongruity, may also be bound to a labeled secondary antibody 38. The physiosorbed labeled secondary antibody 38 thus causes an increased background signal.

Provision of diagnostic tests with a high fidelity is further complicated by the relative scarcity of the target molecules in a particular sample. As reported by Robert F. Service, "PROTEOMICS: Proteomics Ponders Prime Time," *Science* 321, no. 5897 (Sep. 26, 2008): 1758-1761, the concentrations of different proteins in blood varies by more than 10 orders of magnitude. Thus, to ensure a desired level of fidelity, the affinity of the capture molecule to the biomarker of interest must be orders of magnitude higher than the affinity of the capture molecule to any other molecule in the sample.

Overcoming the cross-reactivity and background problems can significantly delay development of a new assay test and can increase the cost and complexity of the overall test. For example, in an effort to mitigate the various sensitivity and interference issues involved with affinity based testing, a particular assay is typically optimized by finding a combination of reagents and environmental conditions that maximizes the binding of the target molecule to the antibody. Thus, optimization can entail incorporating highly selective antibodies. Accordingly, a typical development of an ELISA assay requires several scientists working for more than a year to identify an acceptable antibody. Cross-reactivity of proteins is a common source of the failure of such development efforts.

Another approach for optimizing the diagnostic test for a particular target molecule entails controlling the test conditions locally at different sites of the platform to increase the specificity of the tests. One such approach is described in U.S. patent application Ser. No. 12/580,113, filed on Oct. 15, 2009, the entire contents of which are herein incorporated by reference. Control of the test conditions locally at different sites of the platform can also be used to increase the dynamic range of the assay as described in U.S. patent application Ser. No. 12/688,193, filed on Jan. 15, 2010, the entire contents of which are herein incorporated by reference.

Control of the test conditions locally at different sites of the platform has generally been attempted by electrically influencing biochemical reactions. Various attempts at such electrical control have been reported by R. G. Sosnowski et al., "Rapid determination of single base mismatch mutations in DNA hybrids by direct electric field control," *Proceedings of the National Academy of Sciences of the United States of America* 94, no. 4 (Feb. 18, 1997), Ian Y. Wong and Nicholas A. Melosh, "Directed Hybridization and Melting of DNA Linkers using Counterion-Screened Electric Fields," *Nano Letters* 0, no. 0 (January), Ian Y Wong, et al., "Electronically Activated Actin Protein Polymerization and Alignment," *Journal of the American Chemical Society* 130, no. 25 (Jun. 1, 2008): 7908-7915, and Ulrich Rant et al., "Switchable DNA interfaces for the highly sensitive detection of label-free DNA targets," *Proceedings of the National Academy of Sciences* 104, no. 44 (Oct. 30, 2007): 17364-17369, among others.

Controlling test conditions by electrically influencing biochemical reactions, while promising, has proven problematic to researchers. For example, while influencing test conditions locally at different sites of the platform can increase the specificity of the tests or increase the dynamic range of the assay, most of the electrical potential is dissipated at the electric double layer formed over the electrode surface. Therefore, the electrical influence has a limited range of effectiveness.

A need exists for a device and method of performing an assay incorporating low cost antibodies. A further need exists for tests such as multiplexed assays, e.g., protein arrays, competitive assays, or bead based arrays, as well as low cost devices, e.g., lateral flow devices, or other biochips. Furthermore, methods and compositions for implementing these assays and arrays with higher fidelity would be appreciated. Additionally, methods and devices which provide more accurate results than previous assays would be a further benefit.

SUMMARY

In accordance with one embodiment of the disclosure, a system and method of indirectly modifying an environmental condition at a test site includes providing a test site on a substrate, providing a first activatable stimulant at the test site, providing an actuator configured to activate the first activatable stimulant at the test site, controlling the actuator to activate the first activatable stimulant, and modifying the local chemical environment at the test site with a chemical factor released by the activatable stimulant.

In accordance with another embodiment, a system for controlling an environmental condition at a test site includes a substrate including at least one test site, at least one activatable stimulant on the substrate and configured for use at the at least one test site, and at least one actuator positioned to actuate at least one of the at least one activatable stimulant at the at least one test site.

DESCRIPTION

Figure 1:
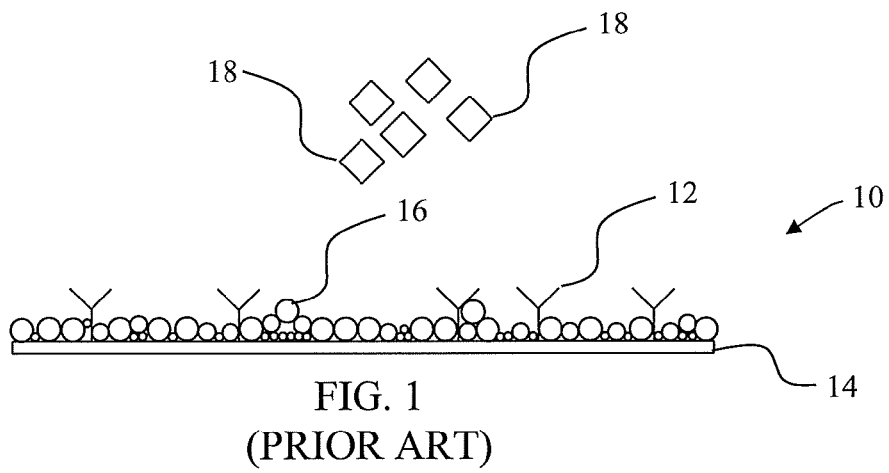
FIG. 1 depicts a schematic of a prior art test site within an ELISA array with an antibody and blockers formed on a substrate as a sample is added to the test site.
Figure 2:
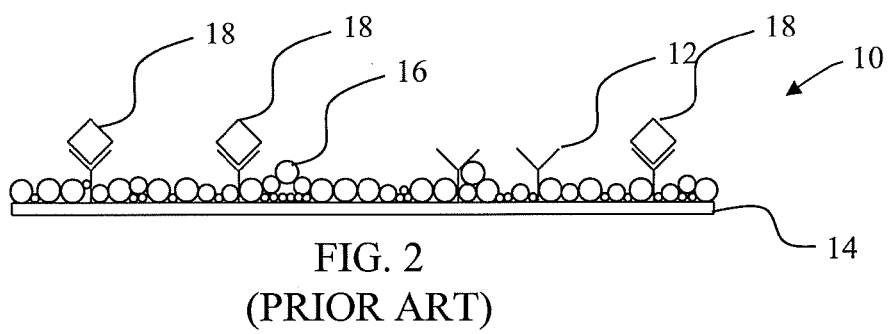
FIG. 2 depicts the test site of FIG. 1 with a target molecule bound to some of the antibodies of FIG. 1 after the test site has been incubated and washed.
Figure 3:
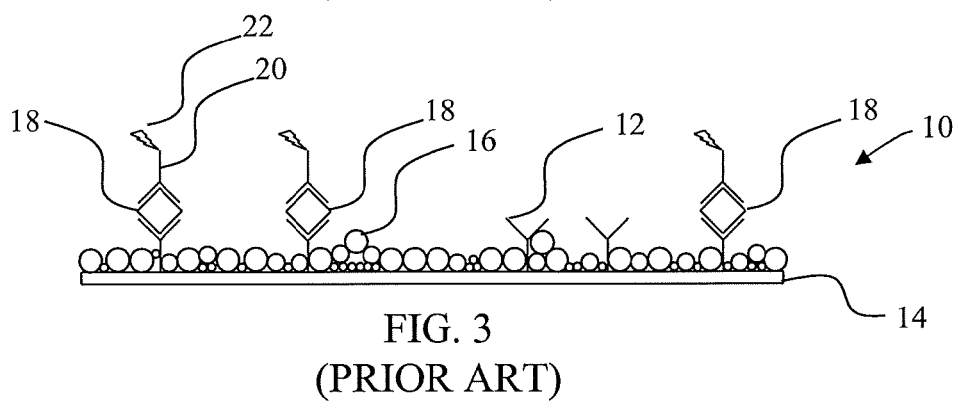
FIG. 3 depicts the test site of FIG. 2 after a labeled secondary antibody has been added and the test site has again been incubated and washed so that the labeled secondary is bound to the bound target molecules.
Figure 4:
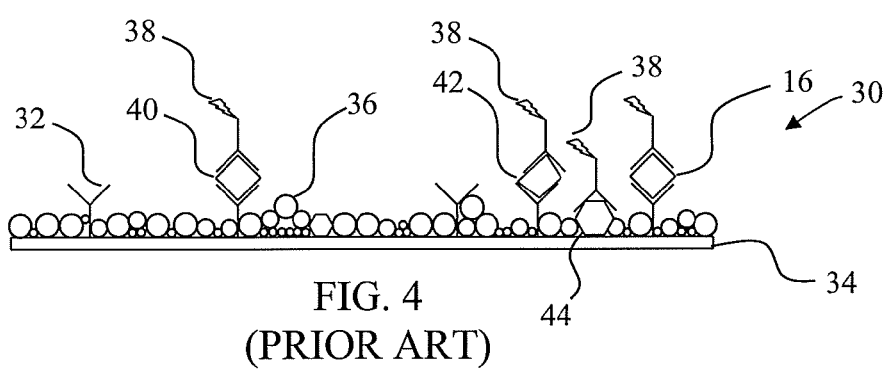
FIG. 4 depicts a schematic of a prior art test site within an ELISA array wherein a labeled secondary is bound to interfering molecules due to cross-reactivity and also physiosorbed to the surface of the substrate raising the background noise level of the test.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 5:
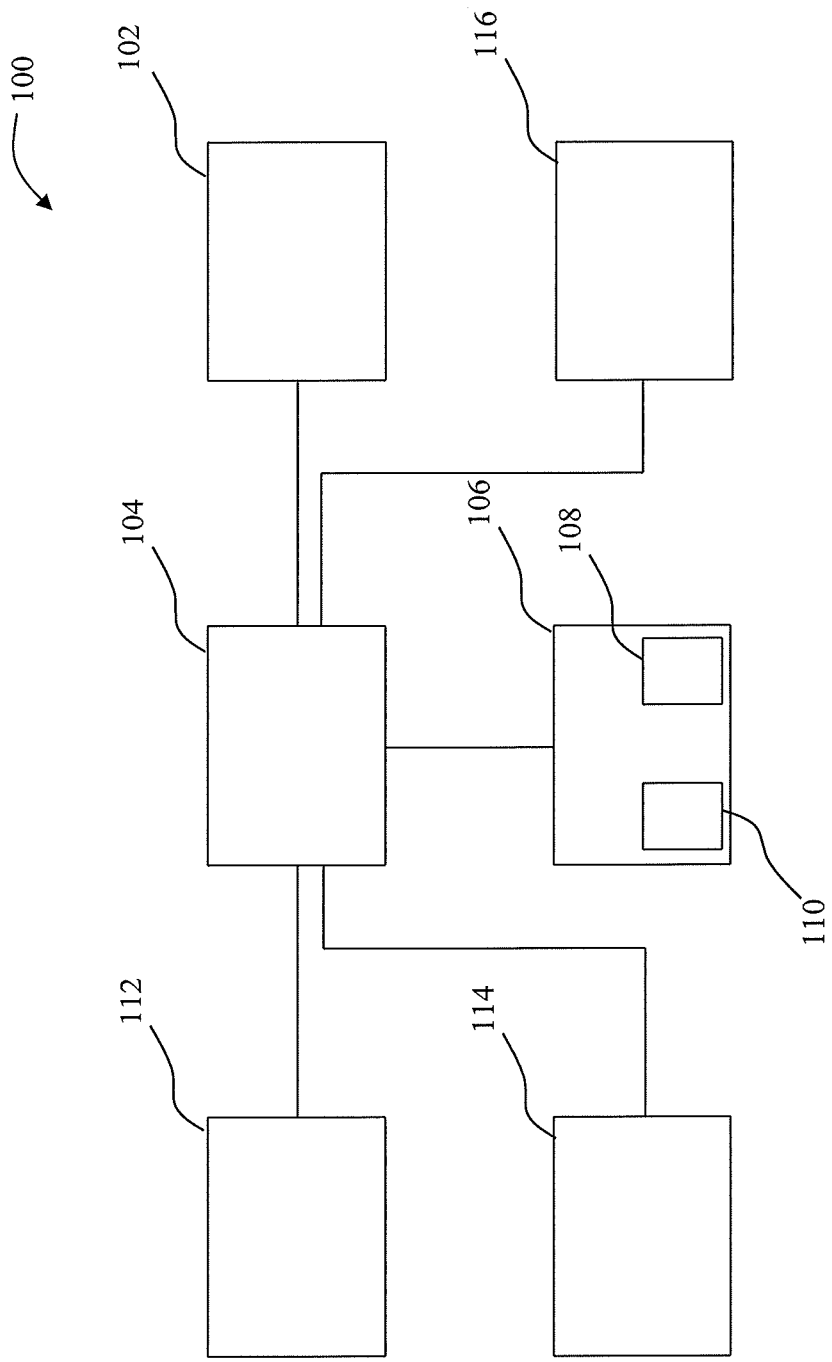
FIG. 5 depicts a multi-site biosensor system configured to control chemical environmental conditions at various test sites to modulate the affinity at the test sites for a target molecule.

Referring to FIG. 5, there is depicted a representation of a multisite biosensor system generally designated 100. The biosensor system 100 includes an I/O device 102, a processing circuit 104 and a memory 106. The I/O device 102 may include a user interface, graphical user interface, keyboards, pointing devices, remote and/or local communication links, displays, and other devices that allow externally generated information to be provided to the biosensor system 100, and that allow internal information of the biosensor system 100 to be communicated externally.

The processing circuit 104 may suitably be a general purpose computer processing circuit such as a microprocessor and its associated circuitry. The processing circuit 104 is operable to carry out the operations attributed to it herein.

Within the memory 106 are various program instructions 108. The program instructions 108, some of which are described more fully below, are executable by the processing circuit 104 and/or any other components of the biosensor system 100 as appropriate. Affinity databases 110 are also located within the memory 106.

The biosensor system 100 further includes chemical environment actuator equipment 112 and chemical environment detector suite 114. The chemical environment actuator equipment 112 is configured to activate an activatable stimulant that affects the chemical environmental conditions at a test site, in this example, within a microarray 120 depicted in FIG. 6. By way of nonlimiting example, one such activatable stimulant is a hydrogel such as those described in Linden, et al., "Stimulus-sensitive Hydrogels and Their Applications in Chemical (Micro)Analysis," *The Analyst*, no. 128 (2003): pp. 325-331, which is incorporated herein by reference in its entirety. It will be appreciated that hydrogels, and particularly biocompatible hydrogels, can be utilized as a selective carrier for a chemical factor selected for its ability to elicit an environmental response that can, for example, increase the sensitivity of a target molecule to a capture molecule. It will be appreciated that various methods may be used to form the microarray platform 120 depicted in FIG. 6, including those methods disclosed in U.S. Pat. No. 5,807,522, incorporated herein by reference in its entirety.

Figure 6:
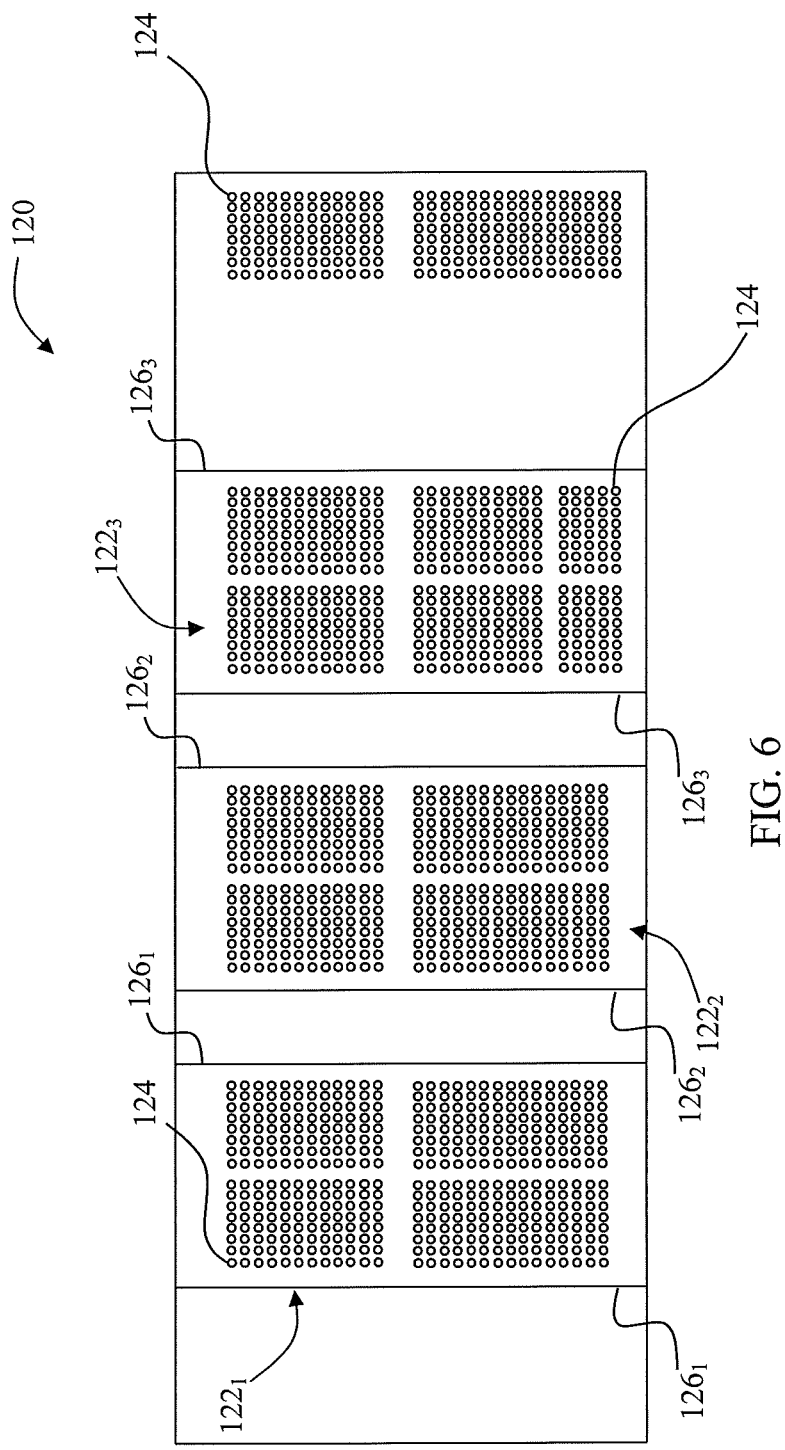
FIG. 6 depicts a platform for providing a number of different test sites in the form of a microarray.

As shown in FIG. 6, a microarray platform 120 includes a number of different subarrays $122_X$. The subarrays $122_X$ include a number of test sites 124. Each of the subarrays $122_X$ is associated with a respective actuator $126_X$. The number and layout of subarrays $122_X$ and associated actuators $126_X$, as well as the number of test sites 124 within each of the subarrays $122_X$ may be varied within the scope of the invention. It will be appreciated that an actuator $126_X$ comprises one or more electrodes, integrated heater, Peltier device, LASER, light source, liquid crystal diode, CMOS, or other device operable to activate a selected activatable stimulant.

According to one embodiment, the selected activatable stimulant comprises a hydrogel operable to selectively retain and release a selected chemical factor. Those chemical factors selected may, by way of nonlimiting example, include biomolecules, pH-altering compounds, buffers, enzymes, antigens, drugs, or other compositions selected for the specific environmental response desired by the practitioner. Alternatively, a hydrogel may be selected for its ability to create bulk fluid flow upon stimulation by the actuator, thereby influencing the flow of components within microarray platform 120.

For example, it will be appreciated that the chemical environment actuator equipment 112 is operable to establish a voltage profile within the microarray platform 120 using electrode pairs as actuators $126_X$. By way of example, the chemical environment actuator equipment 112 is thus used to electrically stimulate one or more hydrogel compositions bonded to a test site 124, and thereby release a chemical factor loaded therein, thereby altering the chemical environment at test site 124 to optimize the conditions for sensing a target molecule. For instance, a chemical factor released by the hydrogel upon stimulation by the electrode pairs as actuators $126_X$ may be a buffer solution operable to modulate the pH of a test site 124 within an ideal affinity range of a target molecule to a capture molecule at test site 124. In practice, stimulation of actuators $126_X$ results in the conformational change of the hydrogel, causing it to deswell and release the buffer solution at a predetermined rate to modulate the pH at each of test site 124. Optionally, the precise pH at test site 124 is detected by a detector suite 114, allowing for feedback to the operator or actuator equipment 112, and further allowing for the modulation of the release of the chemical factor by altering the stimulation presented to the hydrogel. Sensors may be provided on the microarray platform 120 to assist in determining the precise pH within each of the test sites 124.

Referring back to FIG. 5, the system 100 further includes a label reader 116. The label reader 116 may be included in a single device along with the other components of the system 100. Alternatively, one or more of the components of the system 100 may be provided as a separate device which may be remotely located from the other components of the system 100.

As noted above, according to one embodiment, test sites 124 are prepared with a capture molecule effective for selectively binding with a target molecule under preselected environmental conditions. Further details regarding the biosensor system 100 are provided with reference to the procedure 130 of FIG. 7. The processor 104 executes the program instructions 108 to execute at least some of the procedure 130 of FIG. 7. In different embodiments, the procedure 130 may be modified to include more or fewer steps depending upon the specific criterion.

Figure 7:
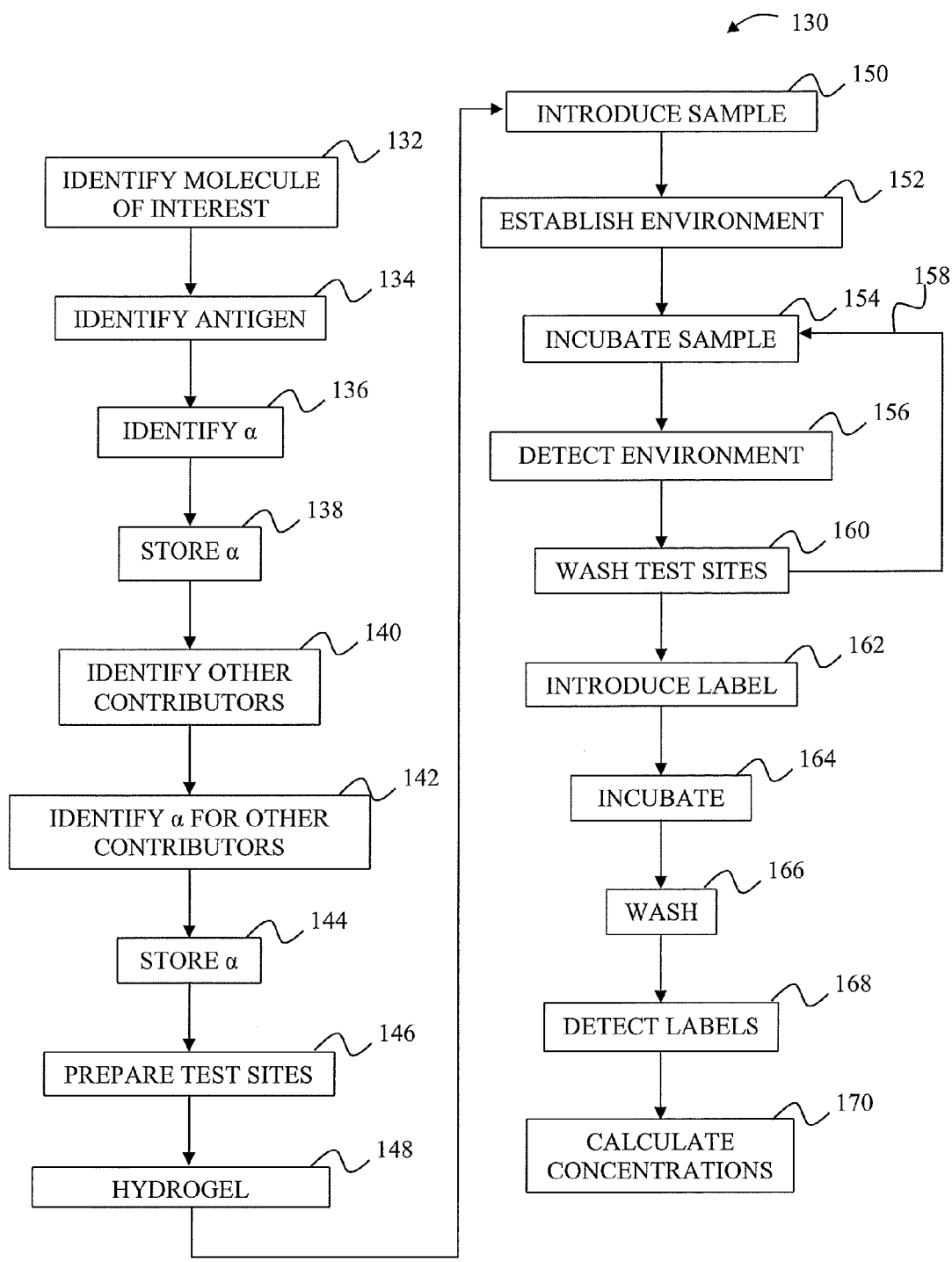
FIG. 7 depicts a procedure that can be used to indirectly establish different test chemical environments at various test sites on a platform so as to expose a sample to multiple test environments.

At block 132 of FIG. 7, a target molecule is identified and then a capture molecule, described herein as an antigen, with an affinity for the target molecule is identified (block 134). A binding efficiency coefficient for the target molecule ($\alpha_t$) with the identified antibody is then identified for at least two different chemical environmental conditions (block 136) and stored in one of the affinity databases 110 (block 138).

Potential sources of test signal interference or noise likely to be present in a tested sample are then identified (block 140). The identification of signal interference may include, for example, an identification of likely or potential molecules within a sample that also have an affinity for the identified capture molecule. A binding efficiency coefficient for each source of noise ($\alpha_n$) with the identified capture molecule is then identified for each of the different chemical environmental conditions (block 142) and stored in one of the affinity databases 110 (block 144).

At block 146, the microarray platform 120 is prepared by depositing the desired amount of the selected capture molecule in each of the test sites 124. In alternative embodiments, a subset of the test sites 124 may be prepared with a first capture molecule while another subset of the test sites 124 may be prepared with a second capture molecule so as to allow two separate tests to be conducted within a single microarray platform 120. Additional configurations within a single microarray platform 120 may also be used. By way of example, each of the test sites within one of the subarrays 122 may be prepared with the same capture molecule while each of the subarrays 122 includes a different capture molecule. The number of test sites 124 prepared with a particular capture molecule in this embodiment is selected to be at least the same as the number of noise sources identified above plus the target molecule.

Once the microarray platform 120 is prepared, a chemical factor is selected for effectuating a selected environmental condition, and a hydrogel for selectively dispersing the chemical factor is loaded with the chemical factor and bonded to microarray platform 120 (block 148). Thereafter, a sample is introduced to microarray platform 120 (block 150), and chemical environment actuator equipment 112 is then controlled to actuate the actuators $126_x$, thereby stimulating the selected hydrogel to release the chemical factors and regulate the environment of the test sites 124 (block 152).

The sample is then incubated at the established test environment for a predetermined time (block 154). During the incubation, the actual test environment within each of the selected set of test sites 124 is monitored by the environment detector suite 114 and data indicative of the established test environment is provided to the processing circuit 104 (block 156).

In one embodiment, data obtained at block 156 is passed to the processing circuit 104 (block 158). Under control of the processing circuit 104, the actuators $126_x$ can be controlled to further modulate the sensed environment at each of the test sites 124. Alternatively, lookup tables may be stored in the memory 106 wherein particular values are associated with electrode voltages for particular concentrations of chemical factors.

When the sample has been sufficiently incubated, the test sites 124 are washed (block 160) and a labeled secondary antibody is introduced into the selected set of test sites 124 (block 162) and incubated (block 164). The selected set of test sites 124 are then washed (block 166) and the labels remaining in the test sites 124 are detected by the label reader 116 (block 168). Based upon the signals associated with the number of labels remaining in the selected set of test sites 124, the concentration of one or more target molecules within the sample is calculated by the processing circuit 104 (block 170).

Figure 8:
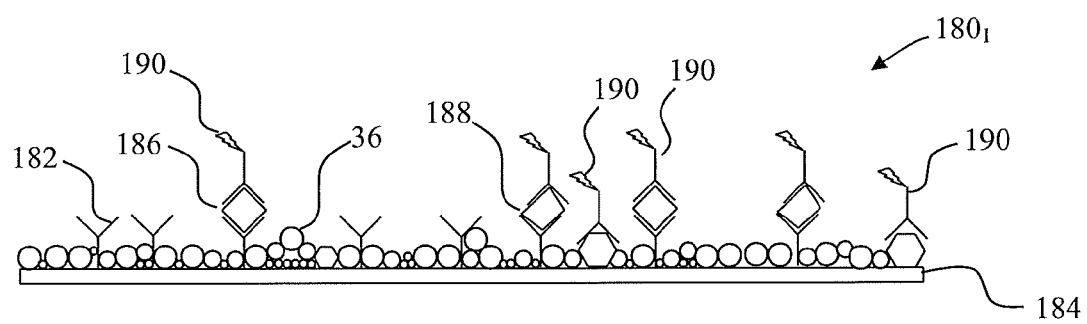
FIG. 8 depicts a schematic of a test site wherein a labeled secondary is bound to target molecules, to interfering molecules due to cross-reactivity, and also physiosorbed to the surface of the substrate raising the background noise level of the test.

Calculation of the concentration of one or more target molecules is possible since the signal obtained by the label reader 116 for a particular one of the selected set of test sites 124 is the summation of the contributors to the signal including the target molecule, and each of the noise sources such as interfering molecules. By way of example, FIG. 8 depicts a test site $180_1$, which, according to certain embodiments, corresponds to test sites 124 described above. As shown herein, a test site $180_1$, includes capture molecule 182 bonded to a substrate 184. In this exemplary embodiment, certain capture molecules 182 have selectively bound to target molecule 186, which is further bound to labeled secondary antibody 190. As shown herein, some interfering antigen 188 has also bound to some of the antibodies 182. A labeled secondary antibody 190 has bound to each of the bound antigens 186 and each of the bound interfering antigens 188. Further, a portion of the labeled secondary antibody 190 has physiosorbed to the blocked surface of the substrate 184.

The relative proportion of the signal attributable to each of the contributors is dependent upon the concentration of the particular contributor, the concentration of the other contributors, and the relative affinity to the initially deposited capture molecule of each of the contributors. The relationship is reflected in the following equation:

$$S_1 = \alpha_{1\text{-}1}C_1 + \alpha_{1\text{-}2}C_2 + \ldots \alpha_{1\text{-}x}C_x$$

wherein $S_1$ is the signal associated with the detected label in the spot $122_1$, $\alpha_{1\text{-}x}$ is the binding efficiency proportional to affinity for the identified contributor (1 through x) at the environment established in spot $122_1$, and $C_X$ is the concentration in the sample of the identified contributor (1 through x).

Accordingly, because the number of the selected set of test sites 124 is equal to at least the number of interfering contributors plus one, the number of detected signals will correspond to the number of identified interfering contributors plus the target molecule. The contribution of the various sources to the overall signal, as well as the value of the overall signal, will vary from test site to test site.

Figure 9:
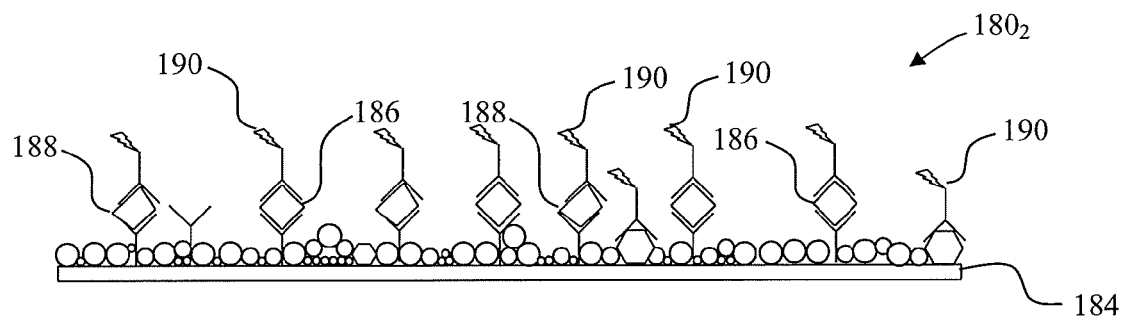
FIG. 9 depicts a schematic of a test site formed identically to the test site of FIG. 8 and exposed to the same sample to which the test site of FIG. 8 was exposed, but maintained at a pH different from the pH of the test site of FIG. 8 during incubation, resulting in different binding efficiencies for the different signal contributors.

By way of nonlimiting example, FIG. 9 depicts a test site $180_2$ which was prepared identically to the test site $180_1$ and exposed to a sample identical to the sample used with the test site $180_1$. The test environment in each of the test sites $180_x$ was different. Accordingly, the labeled secondary antibody 190 bound to the target molecule has increased from two in FIG. 8 to four in FIG. 9. Additionally, the labeled secondary antibody 190 bound to the interfering antigen 188 increased from two in FIG. 8 to three in FIG. 9.

Thus, if three noise contributors are identified in a sample, such as analytes that bind non-specifically to capture molecules sites and prevent the target molecule from binding, analytes that produce erroneous signals, and analytes that physisorb to the surface of the test site and produce erroneous signals, along with the target molecule, four test sites, such as four of the test sites 124, are the minimum number of cells prepared at block 144. Therefore, four signals will be obtained, as reflected in the following equations:

$$S_1 = \alpha_{1\text{-}1}C_1 + \alpha_{1\text{-}2}C_2 + \alpha_{1\text{-}3}C_3 + \alpha_{1\text{-}4}C_4$$

$$S_2 = \alpha_{2\text{-}1}C_1 + \alpha_{2\text{-}2}C_2 + \alpha_{2\text{-}3}C_3 + \alpha_{2\text{-}4}C_4$$

$$S_3 = \alpha_{3\text{-}1}C_1 + \alpha_{3\text{-}2}C_2 + \alpha_{3\text{-}3}C_3 + \alpha_{3\text{-}4}C_4$$

$$S_4 = \alpha_{4\text{-}1}C_1 + \alpha_{4\text{-}2}C_2 + \alpha_{4\text{-}3}C_3 + \alpha_{4\text{-}4}C_4$$

Each term is thus proportional to a binding efficiency factor, $\alpha$, which is a function of the molecule affinities and other assay conditions, e.g., mass transport. Accordingly, because the same sample is used in each of the test sites 124, and because the binding efficiency of the target molecule and the interfering antigens for the specific chemical environment in each of the test sites 124 is known, the procedure 130 provides four equations and four unknowns. The concentrations of each of the contributors can thus be ascertained in a known manner. Accordingly, the concentrations of multiple target molecules within a sample can also be ascertained. In practice the signals are noisy and linear estimation algorithms may be used to estimate the value used for any particular signal. Additionally, one or more sensor sites may be used as a control site to improve the accuracy of the procedure 130.

Accordingly, a chemical factor can be loaded within a hydrogel and included into a bulk solution that includes a sample. When desired, an actuator can then be controlled to trigger the release of the chemical factor from the hydrogel, thereby releasing the chemical factor into the bulk solution so as to modify the chemical environment at a test site.

If desired, the chemical factors loaded into varying hydrogels may be of varying types, each type loaded within a hydrogel with a different activation characteristic. For example, pH buffers of increasing acidity can be loaded within hydrogels having different activation energies. Thus, by changing the activation level of the actuator, a different pH buffer is introduced to the system.

Additionally, other actuators may be used with hydrogel actuators. For example, a LASER or integrated heater can be used to heat thermoresponsive hydrogels, thereby causing the hydrogel to deswell and release a chemical factor preloaded therein. By way of nonlimiting example, a thermoresponsive hydrogel comprising poly(N-isopropylacrylamide) (PNIPAAm) may be selected and loaded with a chemical factor by placing a dried version of the hydrogel in a solution containing the chemical factor in an acetone solution. Thereafter, the chemical factor and hydrogel are allowed to equilibrate for a preselected time—approximately three (3) days according to one embodiment. Thereafter, the hydrogel is prepared according to Dinarvand, "The Use of Thermoresponsive Hydrogels for On-Off Release of Molecules," *Journal of Controlled Release*, vol. 36 (1995), pp. 221-227. Thereafter, according to one embodiment, the chemical factor loaded hydrogel is optionally bonded to a test site 124 in close proximity to an actuator such as a LASER or an integrated heater. It will be appreciated that upon heating of the hydrogel to a lower critical solution temperature by the actuator, the hydrogel releases the loaded chemical factor, thereby modulating the environment of test site 124. As noted previously, the precise environmental condition effectuated by the chemical factor at test site 124 is detected by a detector suite 114, allowing for feedback to the operator or actuator equipment 112, and further allowing for the modulation of the release of the chemical factor by altering the stimulation presented to the hydrogel.

A multisite biosensor can thus be implemented on a printed circuit board, glass, plastic substrate, or on a CMOS chip with gold, glass, epoxy, polymer, or gel coating, or even in a well plate such as a 96 well plate. If desired, control, readout, and also sensing for the control can be provided in the printed circuit board or CMOS chip. CMOS technology allows multiple sensing sites to be fabricated in close proximity. This assists in maintaining uniformity of non-controlled environmental factors amongst the test sites. The chip can be part of a system using stand alone microfluidics or a capillary principle or may be used with a separately provided device. The signal estimation and the assay data can be hard coded on the CMOS chip if desired.

Moreover, the activatable stimulant may be provided on the same substrate as the test site and mixed with the sample as the sample is transported to the test site. For example, a substrate may include a sample receiving area that is linked to a test site by a fluid path. The activatable stimulant may be prepositioned at a location on the fluid path such that the activatable stimulant releases a chemical factor in a manner such that it mixes with the sample as the sample moves toward the test site.

The biosensor system 100 may thus incorporate a variety of activatable stimulants which, when activated, release a preselected chemical factor that modifies the chemical environment of a test site. The particular chemical factor will vary depending upon the particular embodiment and the target molecule selected. Likewise, the type of sensor or sensors incorporated into the label reader 116 will vary depending upon the particular label used. Various embodiments may thus use luminescence, fluorescence, colorimetric, electrochemical, impedance (including electrochemical impedance spectroscopy sensors), and magnetic sensors. The sensors can be configured to allow isolation of the signal produced by a selected one or more test sites. Likewise, the sensors incorporated into the environment detector suite 114 may include IR sensors, and Hall sensors. AMR sensors or GMR sensors may be provided to monitor the density of magnetic beads on a test site surface. ISFETs or CMOS based charge detection circuits may be used in electrochemical embodiments.

The procedure 130 can thus be used in a variety of test site platforms including 96-well plates, plates with fewer or additional wells, microarray platforms, printed circuit board platforms, CMOS chip platforms, multiplexed assays, protein arrays, lateral flow devices, sandwich assays, competitive assays, bead based arrays or other appropriate platforms. The procedure 130 may further be used for the detection of a variety of target molecules as well as different types of molecules in addition to antibodies. By way of example, the procedure 130 may also be used for the detection of nucleic acid, protein, or small molecules. The procedure is not limited to binding processes, and can thus be extended to enzymatic reaction studies including phosphorylation studies, protein-protein interactions, protein nucleic acids interactions, and competitive assays.

Figure 10:
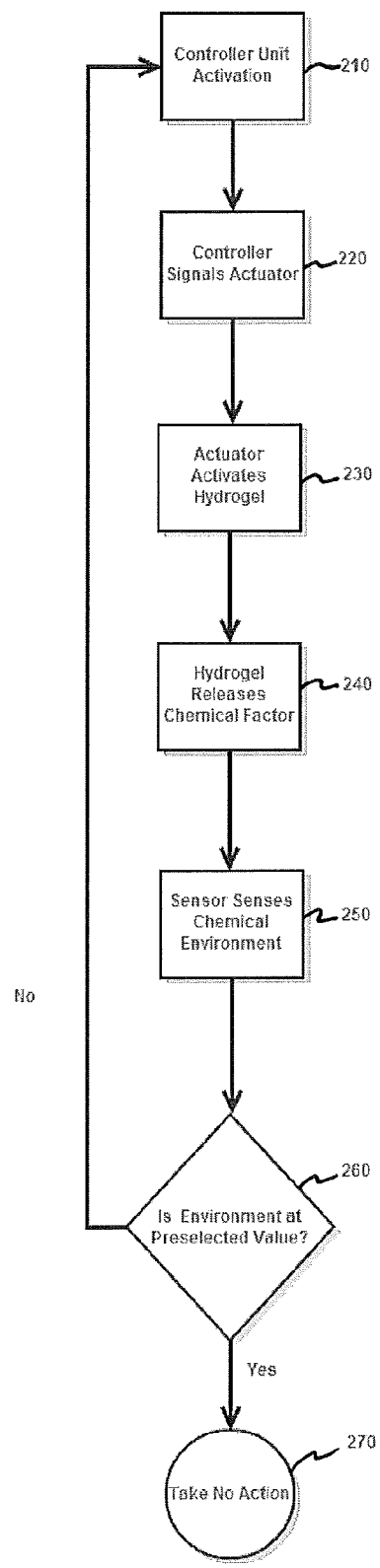
FIG. 10 depicts a procedure that can be used to indirectly establish different test chemical environments at various test sites on a platform to optimize a test environment for detecting a target molecule.

By way of nonlimiting example, an alternative embodiment utilizing biosensor system 100 is provided in FIG. 10. Therein, controller or processor 104 is activated and executes the program instructions 108 (block 210), wherein processor 104 signals the actuator to activate the activatable stimulant (block 220). In this instance, activatable stimulant is a hydrogel loaded with a chemical factor operable to influence the chemical environment at a test site 124. Upon activation of the hydrogel by actuator, the hydrogel releases the chemical factor into the environment surrounding test site 124 (block 230). Thereafter, sensors located near test site 124 sense the chemical environment near test site 124, and send the sensed value to processor 104 (block 250), where processor 104 compares the sensed value to a preselected value correlating to an ideal chemical environmental value for a target molecule's affinity to a capture molecule (block 260). Upon comparing the sensed value to the preselected value or range of values, the processor determines whether additional activation of actuators are necessary (block 210), or whether no further action should be taken other than continued evaluation of the chemical environment.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A method of controlling a test site environment, comprising:
   providing a test site on a substrate with a capture molecule bonded to the substrate and effective for selectively binding with a target molecule under preselected local chemical environmental conditions;
   providing a first hydrogel composition including a first chemical factor at the test site;
   providing an actuator configured to activate the first hydrogel composition to release the first chemical factor at the test site;
   controlling the actuator a first time to activate the first hydrogel composition so as to release the first chemical factor at the test site based upon the preselected local chemical environmental conditions;
   modifying a local chemical environment a first time at the test site with the released first chemical factor;
   sensing the local chemical environment after modifying the local chemical environment the first time; and
   controlling the actuator a second time in response to the sensing of the local chemical environment after modifying the local chemical environment the first time based upon the preselected local chemical environmental conditions.

2. The method of claim 1, wherein providing the first hydrogel composition at the test site comprises providing a pH buffer solution.

3. The method of claim 2, wherein providing the first hydrogel composition at the test site comprises:
preparing a bulk solution including the first hydrogel composition; and
introducing the bulk solution to the test site.

4. The method of claim 3, wherein controlling the actuator a first time comprises heating the first hydrogel composition to at least a lower critical solution temperature.

5. The method of claim 1, further comprising:
providing a second hydrogel composition comprising a second chemical factor at the test site.

6. The method of claim 5, further comprising:
sensing the local chemical environment after controlling the actuator the second time;
comparing the sensed local chemical environment after controlling the actuator the second time with the preselected local chemical environmental conditions; and
controlling the actuator a third time to activate the second hydrogel composition so as to release the second chemical factor based upon the comparison.

7. The method of claim 1, further comprising:
providing a second hydrogel composition comprising a second chemical factor at the test site, the second hydrogel composition having an activation characteristic different from an activation characteristic of the first hydrogel composition.

8. The method of claim 7, further comprising:
sensing the local chemical environment after controlling the actuator the second time;
comparing the sensed local chemical environment after controlling the actuator the second time with the preselected local chemical environment; and
controlling the actuator a third time to activate the second hydrogel composition to release the second chemical factor based upon the comparison.

9. The method of claim 8, wherein controlling the actuator the third time comprises applying power to an electrode on the substrate.

10. The method of claim 6, wherein the first chemical factor and the second chemical factor are the same type of chemical factor.

11. The method of claim 8, wherein controlling the actuator the third time comprises applying heat to the substrate.

12. A method of controlling a test site environment comprising:
providing a test site on a substrate with a capture molecule bonded to the substrate and effective for selectively binding with a target molecule under preselected local chemical environmental conditions;
providing a first hydrogel composition including a first chemical factor at the test site;
providing a second hydrogel composition comprising a second chemical factor at the test site, the second hydrogel composition having an activation characteristic different from an activation characteristic of the first hydrogel composition;
providing an actuator configured to activate the first hydrogel composition to release the first chemical factor at the test site;
controlling the actuator a first time to activate the first hydrogel composition so as to release the first chemical factor at the test site based upon the preselected local chemical environmental conditions; and
modifying the local chemical environment at the test site with the released first chemical factor.

13. The method of claim 12, wherein providing the first hydrogel composition at the test site comprises providing a pH buffer solution.

14. The method of claim 13, wherein controlling the actuator the first time comprises heating the first hydrogel composition to at least a lower critical solution temperature.

15. The method of claim 12, further comprising:
sensing the local chemical environment after releasing the first chemical factor; and
controlling the actuator a second time based upon the preselected local chemical environmental conditions and based upon the sensing of the local chemical environment after releasing the first chemical factor.

16. The method of claim 15, further comprising:
sensing the local chemical environment after controlling the actuator the second time;
comparing the local chemical environment with the preselected local chemical environmental conditions; and
controlling the actuator a third time to activate the second hydrogel composition so as to release the second chemical factor based upon the comparison.

17. The method of claim 16, wherein controlling the actuator the third time comprises applying power to an electrode on the substrate.

18. The method of claim 16, wherein the first chemical factor and the second chemical factor are the same type of chemical factor.

19. The method of claim 18, wherein controlling the actuator the third time comprises applying heat to the substrate.

* * * * *